(12) United States Patent
Schneider

(10) Patent No.: US 8,583,270 B2
(45) Date of Patent: Nov. 12, 2013

(54) GINGIVA FORMER AND METHOD FOR PRODUCING A DESIGN OF A GINGIVA FORMER

(75) Inventor: Sascha Schneider, Mühltal (DE)

(73) Assignee: Sirona Dental Systems GmbH, Bensheim (DE)

( * ) Notice: Subject to any disclaimer, the term of this patent is extended or adjusted under 35 U.S.C. 154(b) by 0 days.

(21) Appl. No.: 13/258,103

(22) PCT Filed: Mar. 24, 2010

(86) PCT No.: PCT/EP2010/053803
§ 371 (c)(1),
(2), (4) Date: Nov. 15, 2011

(87) PCT Pub. No.: WO2010/108935
PCT Pub. Date: Sep. 30, 2010

(65) Prior Publication Data
US 2012/0115105 A1 May 10, 2012

(30) Foreign Application Priority Data

Mar. 24, 2009 (DE) .......................... 10 2009 001 782

(51) Int. Cl.
*G06F 19/00* (2011.01)

(52) U.S. Cl.
USPC .................. 700/98; 700/97; 700/60; 700/61; 700/171; 700/118

(58) Field of Classification Search
None
See application file for complete search history.

(56) References Cited

U.S. PATENT DOCUMENTS

| 4,416,629 | A | * | 11/1983 | Mozsary et al. | 433/174 |
| 5,035,619 | A | * | 7/1991 | Daftary | 433/173 |
| 5,073,111 | A | * | 12/1991 | Daftary | 433/173 |
| 5,145,372 | A | * | 9/1992 | Daftary et al. | 433/173 |
| 5,431,567 | A | * | 7/1995 | Daftary | 433/172 |
| 5,527,182 | A | * | 6/1996 | Willoughby | 433/172 |
| 5,810,592 | A | * | 9/1998 | Daftary | 433/173 |
| 5,873,721 | A | | 2/1999 | Willoughby | |
| 5,989,026 | A | * | 11/1999 | Rogers et al. | 433/172 |

(Continued)

FOREIGN PATENT DOCUMENTS

| DE | 101 50 630 A1 | 4/2003 |
| DE | 103 00 301 A1 | 7/2004 |

(Continued)

OTHER PUBLICATIONS

International Search Report dated Jul. 19, 2010, for PCT/EP2010/053803.

(Continued)

*Primary Examiner* — Kavita Padmanabhan
*Assistant Examiner* — Christopher E Everett
(74) *Attorney, Agent, or Firm* — Fitzpatrick, Cella, Harper & Scinto

(57) ABSTRACT

The invention relates to a gingiva former (1), which has a connecting geometry (5) to an implant (10) and comprises a tailor-made edge (2), a tapering lower part (4) that is located beneath and has a tailor-made shape, and a tapering upper part (8) having a lateral surface (9), wherein the lateral surface (9) has an angle of inclination ($\alpha$) of between 0.5° and 30° with respect to a longitudinal axis (A) of the connecting geometry (5).

8 Claims, 2 Drawing Sheets

(56) References Cited

U.S. PATENT DOCUMENTS

| | | | |
|---|---|---|---|
| 6,120,292 A * | 9/2000 | Buser et al. | 433/173 |
| 6,283,753 B1 * | 9/2001 | Willoughby | 433/172 |
| 6,386,876 B1 * | 5/2002 | Lee | 433/173 |
| 6,788,986 B1 | 9/2004 | Traber et al. | |
| 7,901,209 B2 | 3/2011 | Saliger et al. | |
| 8,033,826 B2 * | 10/2011 | Towse et al. | 433/172 |
| 8,048,345 B2 * | 11/2011 | Feith | 264/19 |
| 2004/0121286 A1 | 6/2004 | Aravena et al. | |
| 2006/0105296 A1 | 5/2006 | Linder et al. | |
| 2007/0037122 A1 | 2/2007 | Bassett et al. | |
| 2007/0111162 A1 * | 5/2007 | Laux | 433/173 |
| 2008/0254412 A1 | 10/2008 | Korrodi et al. | |
| 2009/0087815 A1 * | 4/2009 | Oyama et al. | 433/173 |
| 2010/0003638 A1 * | 1/2010 | Collins et al. | 433/174 |

FOREIGN PATENT DOCUMENTS

| | | |
|---|---|---|
| DE | 20 2007 005 474 U1 | 6/2007 |
| EP | 1 462 066 A2 | 9/2004 |
| EP | 1 745 760 A1 | 1/2007 |
| EP | 2 011 448 A1 | 1/2009 |
| JP | 2007-75532 A | 3/2007 |
| JP | 2007-075532 A | 3/2007 |

OTHER PUBLICATIONS

International Bureau of the World Intellectual Property Organization, "Internationaler Vorlaufiger Bericht Uber Die Patentierbarkeit," issued in connection with International Application No. PCT/EP2010/053803, completed May 31, 2011, 8 pages (and English translation thereof entitled International Preliminary Report on Patentability).

German Patent Office, Examination Report dated Sep. 16, 2009, in connection with German Application No. 10 2009 001 782.8, 4 pages (and machine-generated English translation thereof).

J. Bellmann et al., "Harmonisches Emergenzprofil," Das Dental Labor, No. Apr. 2008, pp. 441-450 (and machine-generated English translation thereof).

English Translation of paragraphs 0021, 0036-0038, 0044, 0059, and 0060 of EP 1 745 760.

Machine translation by Espacenet of EP 1 745 160.

German Examination Report issued by the German Patent Office on Jun. 5, 2012, App. No. 2009 001 782.8.

Machine English translation of the German Examination Report, App. No. 2009 001 782.8.

* cited by examiner

GINGIVA FORMER AND METHOD FOR PRODUCING A DESIGN OF A GINGIVA FORMER

BACKGROUND OF THE INVENTION

1. Field of the Invention

The present invention relates to a healing abutment (such as, e.g., a gingiva former), also referred to as a transgingival healing abutment, and a method for producing a design of a healing abutment (such as, e.g., a gingiva former), in which the healing abutment is attached temporarily to an implant during a healing phase of an implant instead of a customized final implant replacement. Gingival tissue in a preparation area is shaped in a desired manner with the aid of the healing abutment during the healing phase of the implant. In this process, it is important that gingival tissue extending from a shoulder of the inserted implant to an edge thereof assumes a shape that can accommodate the final implant replacement without any gaps or pressure sores and that forms a gingival line on the final implant replacement, namely a break-through line formed on the implant replacement by the gingival tissue, which gingival line coincides with that located on the teeth adjacent to the implant replacement. This is desirable particularly in the region of the front teeth, for esthetic reasons.

2. Description of the Prior Art

Typically, a healing abutment having a standardized geometry has hitherto been screwed onto a freshly inserted implant, where the healing abutment remains during the healing phase of the implant. The term "geometry" is to be understood to mean the outer shape in this context.

The purpose of the healing abutment is to shape the gums as far as possible to give a desired emergence profile following insertion of the final implant replacement, that is to say, the gingival tissue above the implant assumes a shape that matches the gingival line of the other teeth.

It is known from DE 20 2007 005 474 U1 that a healing abutment made of PEEK can be easily adapted and customized mechanically. The first feature of the healing abutment that is customized is the color thereof that is adjusted to match that of the patient's gingival tissue and that imparts a more esthetically appealing appearance to the healing abutment. The above patent specification also discloses that the occlusal portion of the healing abutment can be configured so as to be at an angle in order to make it possible to correct the dental implant axis required for the respective direction of insertion, and to match the circumference of the cylindrical region of the healing abutment to the spatial disposition of the tooth position. Thus the gingiva is shaped during the healing phase in such a way that at least the axis and circumference of the developing cylinder correspond approximately to the axis and circumference of the dental replacement to be subsequently inserted in the region of the gingival tissue.

Moreover, EP 2 011 448 A1 discloses a healing abutment that conditions the oral mucosa in the region of the implant in terms of its shape and position during the healing phase for the prosthetic replacement to be subsequently attached in that the shape and the spatial location of the conditioning surfaces of the healing abutment coincide as precisely as possible with those of the prosthetic replacement in the region of transition to the implant. For this purpose, the contour of the conditioning surface is matched to the inclination of the central axis of the prosthetic replacement. Furthermore, the conditioning surfaces can be provided, in certain areas thereof, with cambers in order to correspond as precisely as possible to the shape of the prosthetic replacement.

Furthermore, it is known from "das dental labor", No. 4/2008, pp 441-450, that a direct transfer of a manually generated customized shape of a healing abutment to a subsequent final implant replacement is possible only when the final implant replacement is likewise fabricated manually.

It would be possible to directly scan the gingival profile up to the implant following the removal of the healing abutment and then to adopt these data for the final implant replacement. However, since it is difficult to scan the gingival tissue optically, the precision with which it is possible to achieve a coincidence between the shape of the gingiva formed by the healing abutment to the shape of the final implant replacement is unsatisfactory.

DE 103 00 301 A1 discloses a further possible way of fitting an implant following the insertion thereof. Instead of a healing abutment, an automatically fabricated superstructure comprising a final abutment and a reduced crown is attached to the implant, the reduced crown being one of reduced size so as to be out of occlusion with the opposing tooth. Thus the reduced crown experiences no transferred forces other than residual forces occurring during the process of chewing, so that the implant is not subjected to stresses. Due to the digital creation of the superstructure, it is very easy to first design the functionally correct crown with the required dimensions and then to compute a size reduction of this crown to ensure that it is reliably disoccluded.

Since the final abutment is in this case fitted to the implant, the gingival tissue in the region adjacent to the implant can shape itself as required for the final implant replacement, and also the edge, that is to say, the break-through of the reduced crown through the gingival tissue will be very similar to the developing emergence profile of the final implant replacement.

However, the disadvantage of this procedure is that, unlike a healing phase during which the implant is covered, the gingival tissue can only grow closer to the initial temporary replacement, i.e., the final abutment and the reduced crown, and there is thus a risk of infections being caused by undesirable foreign bodies coming between the gingival tissue and the initial temporary replacement.

It is an object of the present invention to provide a healing abutment and a method for producing a design of a healing abutment that solves the problems mentioned above.

SUMMARY OF THE INVENTION

The healing abutment (such as, e.g., a gingiva former), also referred to as a transgingival healing abutment, of the invention possessing a connecting geometry for attachment thereof to an implant comprises a customized edge. A tapered bottom portion of the healing abutment located below the edge thereof likewise has a customized shape, and the edge of the healing abutment and the bottom portion located below the same have a shape that corresponds to that of a customized final abutment. A tapered top portion of the healing abutment comprises a circumferential surface that together with a longitudinal axis of the connecting geometry forms a tilt angle ranging from 0.5° to 30°.

The customization of the edge and the bottom portion of the healing abutment located below the edge make it possible to prepare the gum in the region of the implant for a customized final implant replacement by fitting such a healing abutment of the invention to an inserted implant. By virtue of the fact that the healing abutment in the region of the edge and the bottom portion is shaped exactly as the final abutment, the gum surrounding the healing abutment fitted to an inserted implant will assume the shape of the final abutment during the healing phase so that there are no pressure sores or gaps following the removal of the healing abutment and the insertion of the final abutment.

The profile of the edge and the shape of the bottom portion of the healing abutment are configured such that the gum can shape itself during the healing phase of the implant in such a way that an emergence profile is achieved, that is, the profile of the gum extending from the implant shoulder to the breakthrough line formed on the healing abutment by the gum, the so-called gingival line, which emergence profile corresponds to that of the neighboring teeth in order to achieve an as esthetically appealing result as possible. The profile of the edge and the shape of the bottom portion can then be implemented directly for the final implant replacement so that the final emergence profile largely coincides with that of the healing abutment.

The height of the gum above the jawbone of an individual patient is also allowed for by the customized shape of the bottom portion of the healing abutment. Thus as a result of the customized shape of the bottom portion and the edge of the healing abutment of the invention, the top portion thereof, following fitting of the healing abutment to an inserted implant, starts exactly at the level of the gingival line, which is the break-through line formed on the healing abutment by the gum, or even below the same. By virtue of the fact that the top portion is surrounded by gum tissue or it directly adjoins the gingival margin and has a tapered shape, it is possible for the gingival tissue to grow even beyond the edge of the healing abutment during the healing phase, that is, for the healing abutment to become embedded in the gingival tissue in the edge region. During the healing phase, it is typical to observe a gingival regression of from 0.5 mm to 1 mm that is counteracted by the tapered shape of the top portion. As a result, there is a slight surplus of gingival tissue around the final implant replacement following the removal of the healing abutment and the insertion of a final implant replacement, and this surplus gum tissue can be advantageous for the healing process for the final implant replacement. In this context, it is necessary to ensure that this surplus of gum tissue does not displace the profile of the gingival line excessively so that the latter still coincides with the gingival line of the other teeth. This can be controlled via the tilt angle of the top portion of the healing abutment of the invention.

Advantageously, the lateral surface of the tapered top portion has a profile extending in a straight line in the direction of the longitudinal axis and at a constant pitch.

It is thus possible for gingival tissue in the region above the edge of the healing abutment to grow, only in portion, beyond this edge following fitting of the healing abutment to an inserted implant. Thus there is a desirable but not overly excessive surplus of gingival tissue following the removal of the healing abutment and the insertion of the final implant replacement, and this surplus of gingival tissue assists the healing process for the final implant replacement and forms a gingival line on the final implant replacement that matches the gingival line of the other teeth.

Advantageously, the healing abutment is fabricated from plastics-based material.

Since plastics-based materials are plaque-friendly and therefore conducive to a buildup of gingival tissue, the healing process of the gums is accelerated. Since a healing abutment is a provisional and thus temporary replacement, the material used need not exhibit the stability required of a final abutment or for a final implant replacement. Rather, the important factors to be considered when selecting the material are that it should be capable of being very easily and rapidly machined and that it should be moderately cheap.

A further object of the invention is to provide a method for designing a healing abutment possessing a connecting geometry for attachment thereof to an implant, in which method a geometry of a customized final abutment is provided in the form of a 3D data set, by means of design software implemented for the purpose of scheduling an implant replacement, at least in a region that includes the connecting geometry and that is located below an edge of the final abutment. The geometry of the final abutment is used for the geometry of the healing abutment in the region below the edge of the final abutment and for the geometry of the edge itself. The healing abutment is configured so as to be tapered in the region above the edge, and a tilt angle of an external surface of the top portion relative to the longitudinal axis of the connecting geometry is set to be between 0.5° and 30°.

The use of the geometry of the final abutment provided in the form of a 3D data set, at least in a region including the connecting geometry, renders unnecessary any additional process steps for designing the shape of the healing abutment in this region. Only the shape of the healing abutment in the region of the top portion thereof requires an additional designing step.

By the use of the shape of the final abutment for designing the healing abutment in the region of the bottom portion and the edge thereof, it is possible for the gum to form an emergence profile during the healing phase of the implant, which emergence profile corresponds as far as possible to the one desired for the final implant replacement and which matches the emergence profile of the teeth adjacent to the final replacement.

Thus it is possible to make corrections to the emergence profile, when the same does not develop into the desired shape and the gingival line differs from that of the teeth adjacent to the implant. For this purpose, appropriate modifications can be made to the shape existing in the form of a 3D data set, and either a further healing abutment having the appropriately modified shape can be fabricated and inserted, or at least the modified shape in the form of a 3D data set can be used for the purpose of designing an implant replacement.

Advantageously, the healing abutment is designed with the aid of a computer and fabricated by machining.

By the use of a CAD/CAM system, it is possible to design the geometry of the healing abutment with the aid of a computer, to fabricate the same by machining or to adopt the data for fabrication by machining. Furthermore, a final implant replacement can be directly further developed from the 3D data set of the healing abutment of the invention or a final implant replacement can be designed, of which the bottom region can then be implemented directly and supplemented by a top portion corresponding to the healing abutment of the invention. In this way, the gingival line can be determined on a virtual model of the preparation area including the implant and precisely allowed for in the geometry of the healing abutment and the final implant replacement. A method of determining the gingival line on a classical or virtual model is disclosed in "das dental labor", No. 4/2008, pp. 441-450. In conventional technology, the profile of the gingival line is transferred manually to the provisional replacement, which gives rise to inaccuracies. The computer-aided design of the geometry of the healing abutment and the further use of the 3D data set generated in doing so for the customized final implant replacement and the fabrication of the healing abutment and final implant replacement by machining ensure a high degree of precision of coincidence between the shape of the healing abutment and that of the final abutment so that the final emergence profile also corresponds very precisely to the emergence profile formed by the healing abutment.

Furthermore, rapid fabrication of the healing abutment by the dentist is possible when suitable equipment is available.

Advantageously, the geometry of the customized healing abutment is altered stepwise during a healing phase, and the customized healing abutment having the altered geometry is fabricated and inserted between each step.

Thus the gum in the region of an inserted implant can also be adjusted stepwise to match the shape of the final implant replacement.

Advantageously, the edge of the healing abutment corresponds precisely to the gingival line formed by the gum on the customized final implant replacement or it is at a distance from this gingival line such that the gum overlaps the edge of the healing abutment.

As a result, the gum in the edge region of the healing abutment grows over the same during the healing phase. The resulting surplus of gingival tissue following the removal of the healing abutment and insertion of a customized final implant replacement assists the healing process.

Advantageously, the geometry of a final implant replacement is used for the geometry of the healing abutment in the region below the edge and for the geometry of the edge itself, and the final implant replacement can be a single-piece or multi-piece entity.

BRIEF DESCRIPTION OF THE DRAWINGS

An exemplary embodiment of the invention is shown in the drawings, in which.

DETAILED DESCRIPTION OF THE EXEMPLARY EMBODIMENT

Figure 1:
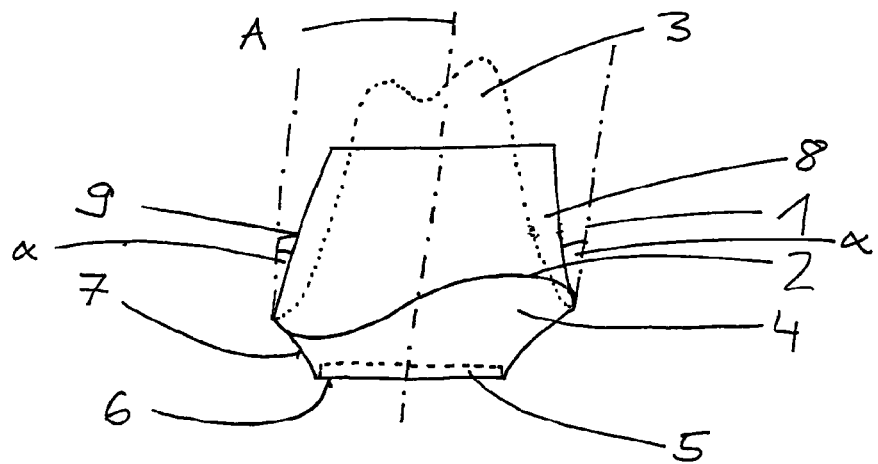
FIG. 1 shows a customized healing abutment of the invention.

FIG. 1 shows a customized healing abutment 1 of the invention. It comprises a customized edge 2 that corresponds to the edge of a customized final abutment 3 indicated by dashed lines.

A bottom portion 4 of the healing abutment located below the edge 2 possesses a connecting geometry 5 for attachment thereof to an implant 10 shown in FIG. 2, which connecting geometry 5 comprises a bottom attachment surface 6 and internal attachment surfaces. The bottom portion 4 further comprises a likewise customized external surface 7 that is disposed between the connecting geometry 5 and the customized edge 2 and that corresponds to the external surface of the customized final abutment 3 in the region below the edge 2.

Thus the bottom portion of the healing abutment is exactly the same as the geometry of the final abutment 3.

A top portion 8 of the healing abutment 1 that is located above the edge 2 is configured so as to be tapered such that a peripheral surface 9 of the top portion 8 and a longitudinal axis A of the connecting geometry 5 form a tilt angle α ranging from 0.5° to 30° at all points. Thus the shape of the healing abutment 1 in the region above the edge 2 differs from that of the final abutment 3. While the final abutment 3 comprises a shoulder, more specifically a camber, directed toward the longitudinal axis A of the connecting geometry, the peripheral surface 9 of the gingival former 1 extends in the exemplary embodiment shown as a straight line in the direction of the longitudinal axis A and at a constant pitch.

Figure 2:
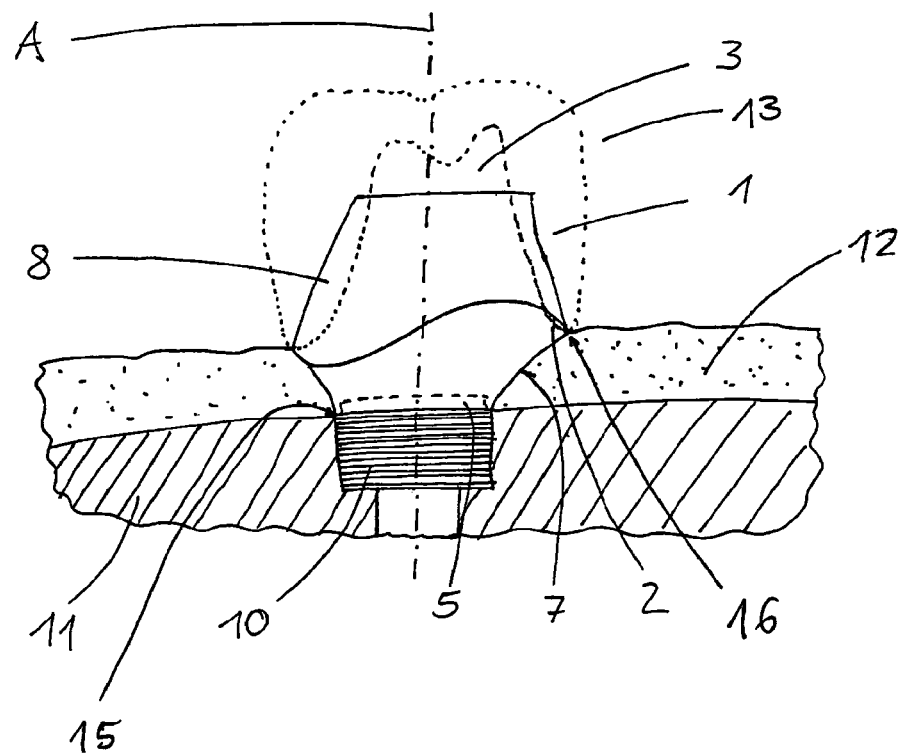
FIG. 2 shows the healing abutment of the invention shown in FIG. 1 that has been fitted to an inserted implant.

FIG. 2 shows the healing abutment 1 attached to the implant 10, which has been inserted into a jawbone 11 in a preparation area of an individual patient, as represented diagrammatically in the figure, and the connecting geometry 5 for attachment to the implant 10 protrudes above the jawbone 11 along the longitudinal axis A, in this exemplary embodiment. The bottom portion of the healing abutment 1 including the connecting geometry 5, the external surface 7, and the edge 2 is surrounded by gingival tissue 12. Following the insertion of the healing abutment 1, the gingival tissue 12 can thus assume a shape corresponding to that of the customized final abutment 3 to be subsequently inserted.

Figure 3:
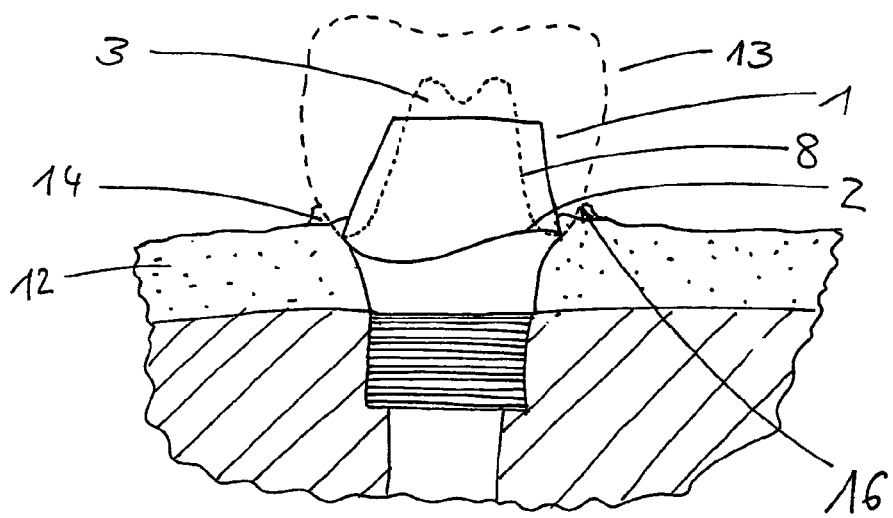
FIG. 3 shows the healing abutment of the invention shown in FIG. 1 that has been fitted to an implant and has healed.

Also, the emergence profile, namely the area between the implant shoulder 15 and the gingival line 16 of the final implant replacement, is formed such that it largely corresponds to the final emergence profile. Only in the region of the gingival line 16 is the emergence profile for the healing abutment caused to deviate somewhat from the final emergence profile by way of the tapered geometry of the top portion of the healing abutment 1. When the healing abutment is inserted, the gingival line 16 either corresponds precisely to the profile of the edge 2 of the healing abutment 1, as shown in FIG. 2, or it overlaps the edge 2 thereof, as shown in FIG. 3. The tapered geometry of the top portion 8 of the healing abutment 1 then enables the gingival tissue to grow laterally to above the edge 2 of the healing abutment 1 during the healing phase.

Thus while the shape of the gingiva 12 in the region of the bottom portion 4 following the removal of the healing abutment 1 corresponds to the shape of the final abutment 3 to be inserted, the tapered top portion of the healing abutment above the edge 2 thereof causes the gingiva 12, on removal of the healing abutment 1 and the insertion of an implant replacement 13, to assume a shape that gives rise to a deviating emergence profile, namely, to a surplus 14 of gingiva 12 all around the implant replacement 13 above the edge 2.

LIST OF REFERENCE NUMERALS OR CHARACTERS 1 customized healing abutment
2 edge
3 final abutment
4 bottom portion
5 connecting geometry
6 bottom attachment surface
7 external surface
8 top portion
9 lateral surface
10 implant
11 jawbone
12 gingiva
13 final implant replacement
14 surplus of gingiva 12
15 implant shoulder
16 gingival line
A longitudinal axis of the connecting geometry
α angle of inclination

The invention claimed is:

1. A method for producing a design of a gingiva former having a connecting geometry for attachment thereof to an implant during a healing phase, comprising:
providing a geometry, including a connecting geometry, of a customized final abutment as a 3D data set at least in a lower region of the final abutment, the lower region of the final abutment being defined by an edge of the final abutment and by the connecting geometry below the edge of the final abutment, the final abutment being constructed for attachment to the implant subsequent to removal of the gingiva former from the implant;

generating a geometry of a lower region of the gingiva former based on the geometry of the final abutment, wherein the lower region of the gingiva former is defined by an edge and a connecting geometry below the edge that respectively correspond to the edge of the final abutment and the connecting geometry of the final abutment, wherein the geometry of the gingiva former is generated with a computer and fabricated by machining, wherein said edge of said gingiva former exactly corresponds to a break-through line of the final abutment formed by gingiva or is at a distance from the break-through line such that gingiva overlaps said edge of said gingiva former, wherein the geometry of the customized final abutment is based on geometry of a preparation area of a patient's mouth, the preparation area being in either modified or unmodified form, and wherein the customized final abutment and the gingiva former are distinct physical objects.

2. The method as defined in claim 1, wherein the geometry of said customized gingiva former is altered stepwise during the healing phase and the customized gingiva former is fabricated and inserted with altered geometry.

3. The method as defined in claim 1, wherein the geometry of a final implant replacement is used for the geometry of said gingiva former in the region below said edge and for the geometry of said edge and the final implant replacement can be a single-piece or multi-piece entity.

4. The method as defined in claim 1, further comprising generating a geometry of an upper region of the gingiva former, wherein the upper region is defined by a tapered surface extending from the edge of the gingiva former in a direction away from the lower region, said surface being tapered inwardly away from the lower region.

5. The method as defined in claim 4, wherein the tapered surface is angled from 0.5° to 30° relative to a longitudinal axis of the connecting geometry of the gingiva former.

6. The method as defined in claim 1, wherein the geometry of the customized final abutment is based on a virtual model of the preparation area.

7. The method as defined in claim 1, further comprising generating the geometry of the customized final abutment as a virtual model of a preparation area of a patient's mouth.

8. The method as defined in claim 1, further comprising fabricating the gingiva former at least from the geometry of the lower region of the gingiva former.

* * * * *